United States Defensive Publication [19] (H) [11] T965,005

Leone et al. [43] Dec. 6, 1977

[54] NUCLEATING AGENTS, RADIATION-SENSITIVE COMPOSITIONS AND PHOTOGRAPHIC ELEMENTS

[76] Inventors: Ronald E. Leone; James K. Elwood, both c/o Kodak Park Division, Rochester, N.Y. 14650

[21] Appl. No.: 768,519

[22] Filed: Feb. 14, 1977

Related U.S. Application Data

[62] Division of Ser. No. 700,981, June 29, 1976.

[51] Int. Cl.$^2$ ..... C09B 23/00; C07D 275/04

[52] U.S. Cl. ..... 542/429; 260/304 D

[57] ABSTRACT

Heterocyclic N-(acylhydrazinophenyl)thioamide nucleating agents are disclosed as well as radiation-sensitive compositions and elements containing such nucleating agents in combination with silver halide grains capable of forming an internal latent image. The elements can be used to form direct-positive photographic images. Dye image transfer photographic elements are specifically contemplated. A specifically preferred compound class comprised of a combination of preferred moieties can be indicated by the formula:

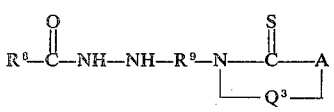

(IV)

wherein:

A is $=N-R^2$, —S— or —O—;

$Q^3$ is represented by the formula

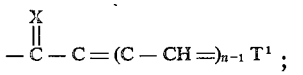

X is $=S$ or $=O$;

$T^1$ is

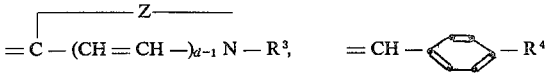

or $-H_2$;

$R^3$ is an alkyl substituent;

$R^4$ is hydrogen, an alkyl,

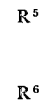

or an alkoxy substituent;

Z represents the non-metallic atoms necessary to complete a basic 5- or 6-membered heterocyclic nucleus of the type found in cyanine dyes having ring-forming atoms chosen from the class consisting of carbon, nitrogen, oxygen, sulfur and selenium;

*n* and *d* are independently chosen from the integers 1 and 2;

$R^8$ is hydrogen, phenyl, methyl, ethyl, propyl or butyl;

$R^9$ is a meta- or para-phenylene group;

$R^2$, $R^5$ and $R^6$ are independently chosen from hydrogen, phenyl, alkyl, alkylphenyl and phenylalkyl; and the alkyl moieties in each instance include from 1 to 6 carbon atoms.

to complete the Abstract.

6 Claims, No Sheets Drawing,

88 Pages Specification

The file of this unexamined application may be inspected and copies thereof may be purchased (849 O.G. 1221, Apr. 9, 1968).